United States Patent
Rashid et al.

[11] Patent Number: 5,770,224
[45] Date of Patent: Jun. 23, 1998

[54] CAPSULE CONSTRUCTION

[75] Inventors: Abdul Rashid, Glasgow; Howard Norman Ernest Stevens, Drymen; Massoud Bakhshaee, Glasgow; James Robertson Miller Kelso, Dalry; Mark Hegarty, East Kilbride, all of United Kingdom; James Leonard Mackie, Windsor, Canada

[73] Assignee: R. P. Scherer Corporation, Troy, Mich.

[21] Appl. No.: 433,334

[22] PCT Filed: Nov. 4, 1993

[86] PCT No.: PCT/GB93/02270

§ 371 Date: Jun. 26, 1995

§ 102(e) Date: Jun. 26, 1995

[87] PCT Pub. No.: WO94/09745

PCT Pub. Date: May 11, 1994

[30] Foreign Application Priority Data

Nov. 4, 1992 [GB] United Kingdom ............... 223172

[51] Int. Cl.$^6$ ................................................ A61K 9/48
[52] U.S. Cl. .............. 424/451; 220/8; 220/DIG. 34; 424/453; 424/454
[58] Field of Search .................. 424/451, 452, 424/453, 454, 456; 220/8, 796, DIG. 34; D24/104

[56] References Cited

U.S. PATENT DOCUMENTS

| | | | |
|---|---|---|---|
| 2,340,037 | 1/1944 | Zipper | 167/83 |
| 3,584,759 | 6/1971 | Lorincz | 220/780 |
| 3,927,195 | 12/1975 | Messora | 424/454 |
| 3,959,540 | 5/1976 | Leiberich et al. | 428/35.7 |
| 4,487,327 | 12/1984 | Grayson | 220/8 |
| 4,667,498 | 5/1987 | Sauter | 72/108 |
| 4,793,493 | 12/1988 | Makiej, Jr. | 206/538 |

FOREIGN PATENT DOCUMENTS

| | | |
|---|---|---|
| 0246804 | 5/1987 | European Pat. Off. . |
| 0274345 | 11/1987 | European Pat. Off. . |
| 2232236 | 1/1974 | Germany . |
| WO9213521 | 8/1992 | WIPO . |

*Primary Examiner*—George F. Lesmes
*Assistant Examiner*—Robert H. Harrison
*Attorney, Agent, or Firm*—Gifford, Krass, Groh, Sprinkle, Patmore, Anderson & Citkowski, P.C.

[57] ABSTRACT

A controlled release capsule comprises a male plug (2) formed of a water swellable hydrogel which is engaged within a neck portion (4) of a female body (6). The capsule contains a pharmaceutically active material. In contact with an aqueous medium, such as in the gastrointestinal tract, the hydrogel plug swells and becomes disengaged from the body, thereby releasing the active material. In order to facilitate insertion of the male plug into the neck of the body, the body has a flared mouth portion (14) which is wider than the neck. The neck itself may be wider or narrower than the remainder of the body. A water-soluble cap (8) has detentes (18) which clip over the flared mouth portion so as to lock the cap thereto.

8 Claims, 2 Drawing Sheets

CAPSULE CONSTRUCTION

TECHNICAL FIELD

The present invention relates to a controlled release capsule construction intended for containing a pharmaceutically active material, which comprises a male member engaged within a neck portion of a female body; the capsule including a water swellable material which swells so as to disengage the female body upon exposure of the capsule to an aqueous medium.

BACKGROUND

International Patent Specification WO 90/09168 discloses a device of this type which comprises a water swellable male plug engaged within a female body. A pharmaceutically active material is contained within the device. When the capsule is exposed to water, the male hydrogel plug swells and eventually disengages itself from the female body, thereby allowing the pharmaceutically active material contained within the device to be released. It has been found that the time taken to release the pharmaceutical material is predictable and reproducible, so that the device may be used to release pharmaceutically active materials within the body of a patient after a predetermined time interval (e.g. 0.5 to 12 hours). This may, for example, be useful in the treatment of medical conditions where it is desirable to administer a pharmaceutically active material to the patient sometime through the night, while the patient is asleep, so as to provide a desired level of the drug in the patient in accordance with his needs, for example during the night or when he awakes. It may also be useful to allow dosing of materials at a predetermined point as the capsule passes through the gastro-intestinal tract, for example in the colon.

Patent specification WO92/13521 (Alza Corporation) describes fluid-imbibing dispensing devices for delayed delivery of an active agent, which include an expansion means which absorbs fluid from a surrounding environment. The dispensing device comprises a housing having first and second wall sections telescopically engaged with each other, particularly a capsule having a hollow cap and a hollow body; either the cap or the body is in the form of a male section fitted inside the open end of the other female section. The expansion means is contained within the device and expands as it absorbs fluid, forcing apart the two sections of the device. The expansion means may be a swellable polymer or an osmotic formulation which swells as it absorbs fluid. In order to allow fluid to come into contact with the expansion means contained within the device, one of the wall sections adjacent to the expansion means is fluid-permeable. After the sections are disengaged, fluid enters the device and comes into contact with the active agent contained within the device, thereby dispensing the active agent into the fluid.

Conventional hard gelatin capsules are produced and filled in large numbers using high speed automatic machinery. Such capsules comprise a body and a cap. Normally the cap is pre-fitted to the capsule body during manufacture of the capsule. During filling, the filling machine removes the cap, fills the capsule with pharmaceutical material, and then replaces the cap in a manner such that the cap is locked onto the capsule body. Patent Specification U.S. Pat. No. 3,399,803 discloses a self-locking medicament capsule wherein the body has a groove near its open end, and the cap has a corresponding ridge which snags into the groove so as to lock the cap and body together. U.S. Pat. No. 4,442,941 discloses a bayonet-type arrangement whereby a raised portion on the cap is engaged into a groove on the body.

European Patent Specification 246804 also discloses a capsule body having a groove near its mouth for the purposes of preventing the capsule distorting from its cylindrical form, which may cause difficulty in fitting the cap onto the capsule body.

A preferred embodiment of the controlled release capsule with which the present invention is concerned (and as disclosed in WO 90/09168) requires that a male hydrogel plug be a close fit within the neck of the female capsule body so that the plug is firmly retained and does not detach prematurely.

The hydrogel plug prior to hydration is a fairly rigid material. For these reasons, it may be difficult to insert the tightly fitting hydrogel plug into the mouth of a conventional cylindrical capsule body using high speed machinery. If the body is slightly oval, or the plug and body are not perfectly aligned, there is a danger that the plug will crush or crack the mouth of the capsule body during insertion.

It is an object of the present invention to mitigate this problem.

SUMMARY OF THE INVENTION

The present invention provides a controlled release capsule which comprises a male member engaged within a neck portion of a female body; the capsule including a water swellable material which swells so as to disengage the female body upon exposure of the capsule to an aqueous medium; the body comprising a flared mouth portion adjacent the neck portion, the mouth portion having an entrance which is wider than the neck portion and wider than the male member so as to facilitate insertion of the male member into the neck portion; and the neck portion of the female body being narrower than the remainder of the body.

The flared mouth portion provides a ramped lead-in, so that the male member may be inserted readily into the neck of the female body. Usually, the mouth portion is flared at an angle of 10° to 60° (preferably 15°–45°) to the line of the capsule. In order to facilitate initial positioning of the male member prior to insertion into the body, the flared mouth member may be belled out into a substantially cylindrical entrance portion adjacent the entrance to the body, which is normally of substantially the same diameter as the female body.

Usually, the capsule body and the neck portion thereof are of substantially cylindrical configuration according to conventional practice.

In addition to the flared mouth portion, in one embodiment the neck portion is narrower than the remainder of the body. This enables the flared mouth portion to still be within the overall diameter of the capsule body. A flared mouth portion extending beyond the line of the capsule body may pose problems in handling using high speed filling machinery. Recessing the neck portion in this way may also contribute to the overall strength of the neck portion and minimises splitting. Preferably, the neck portion has a diameter which is 80% to 99% (usually 90 to 98%) of the diameter of the female body. Furthermore, it is preferred that the maximum diameter of the entrance of the flared mouth portion be substantially the same as the diameter of the female body itself.

Preferably, the capsule body is prepared by conventional capsule forming techniques, which involve dipping a mould pin in a solution of the material (such as gelatin) from which the capsule is to be formed. Spraying could be used instead of dipping. The gelatin is then dried and stripped from the pin. The capsule body may then be trimmed as necessary. The presence of a narrow neck portion which is narrower than the body makes it somewhat more difficult to strip the capsule body from the mould pin, compared to conventional cylindrical capsules. Alternatively, the capsule might be made by other known capsule manufacturing techniques, such as injection moulding of thermoplastic materials.

The walls of the female body may be formed from a wide variety of materials. They may be of homogenous constructions or they may be laminated. Examples of materials suitable for use in the construction of the body include polyethylene, polypropylene, poly(methylmethacrylate), polyvinyl chloride, polystyrene, polyurethanes, polytetrafluoroethylene, nylons, polyformaldehydes, polyesters, cellulose acetate and nitro cellulose.

However, a preferred construction uses an impermeable coating to cover the exterior of a body which has been formed from a water soluble material. The coating may conveniently be formed by dipping the body in a solution of a material which forms a layer which is impermeable to water. Alternatively, the body might be spray-coated. A preferred class of capsule bodies are conventional hard gelatin or starch capsule bodies coated with a solution of polyvinyl chloride or a polyvinyl acetate copolymer or an ethyl cellulose solution.

In a preferred embodiment, the male member is a plug; usually of cylindrical configuration. The plug is formed of the water swellable material, which is preferably a hydrogel. As it absorbs water, the hydrogel plug swells and becomes disengaged from the female body. The hydrogel is preferably a water swellable material as disclosed in patent specification WO90/09168.

Usually the neck portion is substantially cylindrical, so as to form a tight fit with the cylindrical male plug.

In another embodiment, the male member is a hollow member closed at one end, whose opposite open end engages within the neck of the female body. A water swellable material is provided within the capsule which serves to disengage the female body after a predetermined time, by forcing the male member and the female body apart as the material swells in the presence of water. The swellable material inside the capsule may be an osmagent or an osmopolyer. Such an arrangement is disclosed in WO92/13521. In order to allow water to enter the capsule and to contact the water-swellable material a portion of the wall of the capsule adjacent thereto is preferably semipermeable; that is to say it is permeable to the passage of water into the device but impermeable to release of other substances from within the capsule.

Another aspect of the invention relates to a process of filling the capsule, which comprises storing caps and bodies separately, filling a body with active material, inserting the male member into the neck of the body, and fitting a cap over the open end of the body.

DETAILED DESCRIPTION OF PREFERRED EMBODIMENTS

Figure 1:
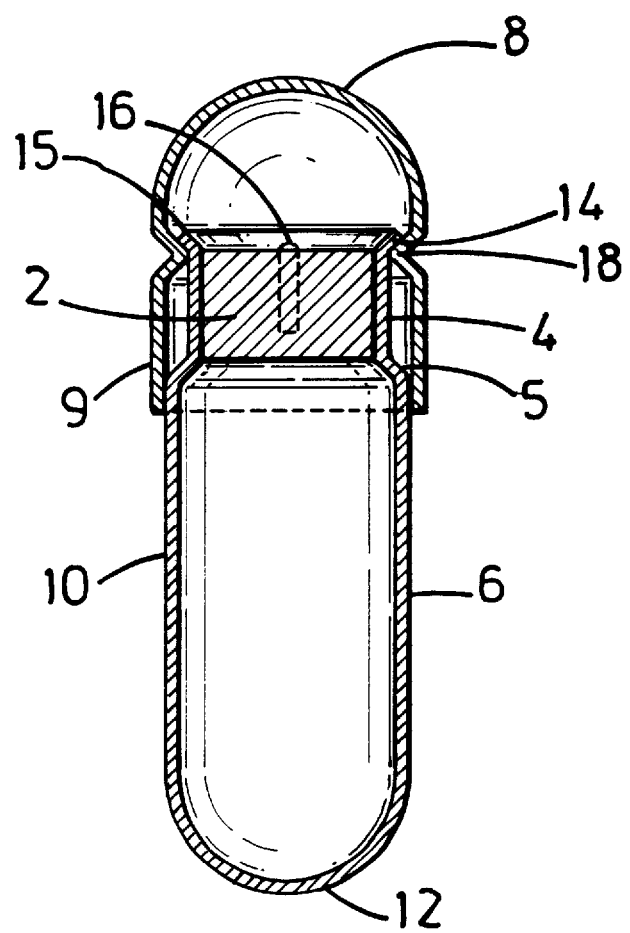
FIG. 1 is a cross-sectional view of a first embodiment of a controlled release capsule structured in accord with the principles of the present invention.
Figure 2:
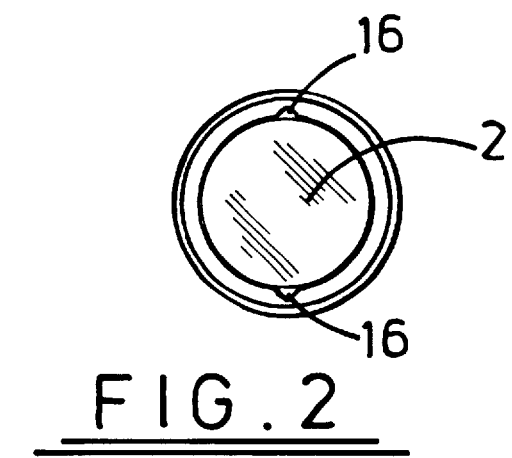
FIG. 2 is a top view of the capsule of FIG. 1, having the cap portion removed.

Embodiments of the present invention will now be described by way of example only in conjunction with the drawings wherein:

FIG. 1 is a cross-sectional elevation of a first embodiment;

FIG. 2 is a view from above with the cap removed; and

Figure 3:
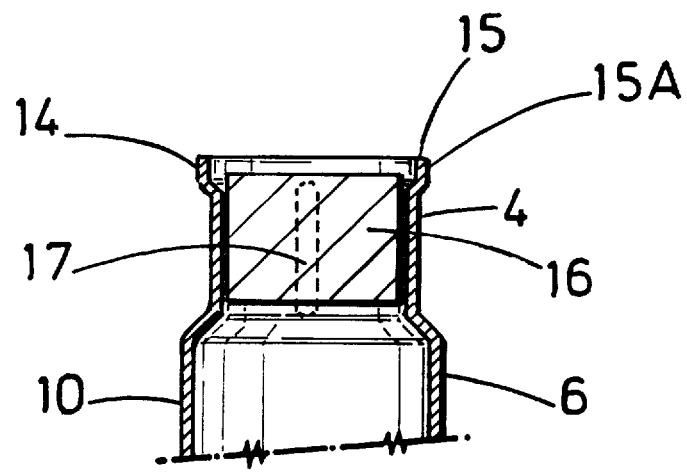
FIG. 3 is a partial, elevational view of a second embodiment of capsule structured in accord with the principles of the present invention.
Figure 4:
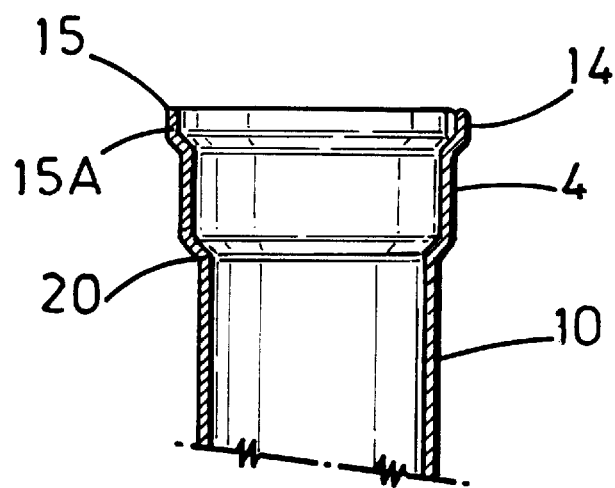
FIG. 4 is a partial, elevational view of a fourth embodiment of capsule structured in accord with the principles of the present invention.

FIG. 3 is a partial elevational cross-section of a second embodiment.

The capsule shown in FIGS. 1 and 2 comprises a male member in the form of a plug 2 formed of a hydrogel material, inserted in neck 4 of female body 6. The capsule is closed with a cap 8.

The body 6 comprises a cylindrical main portion 10 and closed end 12. The main body narrows to the neck portion 4 at a shoulder region 5. The neck portion is substantially cylindrical so as to receive the male plug 2 with a close tolerance. The neck portion then flares out to a flared mouth portion 14 which has an entrance 15 of a diameter substantially the same as the diameter of the main body portion 10.

The cylindrical neck portion is advantageously provided with a vent channel 16 shown in dotted lines which extends from the flared mouth portion part way down the neck portion and allows the release of pneumatic pressure from within the capsule body during insertion of the plug. However, the vent channel extends only part way down the neck portion, so that when the plug is fully inserted into the neck, it seals with the lower region of the neck where the vent channel is absent. As shown in FIG. 2, a vent channel 16 may be provided on either side of the neck as required.

The male plug 2 is formed of a hydrogel material (such as disclosed in WO 90/09168) and is usually inserted so that the upper end of the plug is level with or below the upper end of the capsule body.

The capsule is then sealed with the cap 8 which is provided with detentes 18 which clip under the rim of the flared mouth portion thereby locking the cap in place.

The cap has a cylindrical skirt portion 9 which extends down to the open end of the cap. The lower end of the skirt portion extends downwardly past the shoulder 5 of the body and encloses an upper part of the body with only a small clearance. This helps to stabilise the cap and prevent it tilting from side-to-side. It also allows the cap to be sealed to the body by means of an annular band passing over the junction therebetween.

The cap is formed of a water soluble material, such as gelatin. The capsule body is formed of a water insoluble material, which may be a water insoluble plastics material or may be gelatin coated with a water-impermeable coating.

The capsule body is formed in conventional manner by dipping a mould pin into a gelatin solution and allowing to dry. The gelatin is then coated with a water-impermeable coating (e.g. by dip-coating) after the capsule body has been stripped from the mould pin and trimmed to size. Alternatively, the water-impermeable coating may be applied by spray coating or vapour deposition. The cap 8 is then temporarily fitted over the capsule body such that the detentes 18 do not lock over the rim of the flared mouth portion. The pre-assembled empty capsule is then stored for later filling. During filling, the cap is removed from the capsule body, and a pharmaceutically active material is filled into the capsule body. The hydrogel plug is then fitted into the neck of the body. Finally, the cap is replaced over the end of the capsule body and pushed down so that the detentes 18 clip over the rim of the flared mouth portion, thereby locking the cap in place.

However, the preassembly step is not essential. The caps and bodies may be stored separately and fed separately to the filling machine, particularly if precautions are adopted to prevent the caps nesting together and the bodies nesting during storage and feeding in the filling machine. The narrow neck construction shown in FIG. 1 helps minimise nesting of the bodies. A flattened cap shape, increased width of the dome of the cap, or increased cap wall thickness helps minimise nesting of caps.

When the capsule is administered to a patient, the aqueous environment in the gastrointestinal tract quickly dissolves the water soluble cap. Water is then absorbed into the hydrogel plug 2, which swells and is expelled from the body after a predetermined time interval (for example 2 to 10 hours). This allows the contents of the capsule to be released into the patient's gastro-intestinal tract.

FIG. 3 shows a second embodiment which is similar to the first embodiment, except as regards the shape of the flared mouth portion and the extent of the vent channel. The cap is omitted for simplicity.

Thus, the vent channel 17 extends through the full length of the cylindrical neck portion, so that even when the plug is fully inserted, a total seal is not achieved. Such a construction may be easier to demould than the shorter channel shown in the previous embodiment.

The flared mouth portion 14 is belled outwardly, such that the entrance region 15A to the body portion is substantially cylindrical and of a diameter substantially the same as that of the main portion 10. This facilitates location of the plug in the mouth of the body prior to being fully inserted.

Whether the plug is inserted proud of the neck portion, flush with the upper end neck portion, or is recessed below the upper end of the neck portion can affect the time taken to expell the plug. This time will be chosen according to the desired release time of the capsule contents.

We claim:

1. A controlled release capsule which comprises a male member (2) engaged within a neck portion (4) of a water-impermeable female body (6); the capsule including a water swellable material which swells so as to disengage the female body upon exposure of the capsule to an aqueous medium;

the female body comprising a flared mouth portion (14) adjacent the neck portion, the mouth portion having an entrance (15) which is wider than the neck portion and wider than the male member so as to facilitate insertion of the male member into the neck portion; and the neck portion of the female body being narrower than the remainder of the body; and the male member comprising a plug, and the plug being formed of said water swellable material.

2. A capsule according to claim 1 wherein the neck portion of the female body is substantially cylindrical.

3. A capsule according to claim 1 wherein the mouth portion (14) is flared at an angle of 10° to 60° to the longitudinal direction of the neck portion.

4. A capsule according to claim 1 wherein the flared mouth is belled out into a substantially cylindrical entrance portion (15).

5. A capsule according to claim 4 wherein the substantially cylindrical entrance portion is of substantially the same diameter as the female body.

6. A capsule according to any preceding claim wherein the female body and the neck portion are substantially cylindrical and the neck portion has a diameter which is 80 to 99% of the diameter of the female body.

7. A capsule according to claim 1 which further comprises a cap (8) of a water soluable material, the cap having inwardly extending protrusions (18) which clip over the flared mouth portion (14) of the female body to lock the cap in place on the female body.

8. A capsule according to claim 7 wherein the neck portion of the female body is substantially cylindrical; and wherein the cap has an open end and a skirt portion (9) adjacent thereto, the skirt portion enclosing a party of said remainder of the female body.

* * * * *